United States Patent [19]

Ohkawa

[11] Patent Number: Plant 6,599

[45] Date of Patent: Feb. 14, 1989

[54] ROSE PLANT NAMED 'DEVALE'

[75] Inventor: Kiyoshi Ohkawa, Shizuoka, Japan

[73] Assignee: Kanagawa Prefecture, Yokohama, Japan

[21] Appl. No.: 57,443

[22] Filed: Jun. 1, 1987

[51] Int. Cl.[4] ..... A01H 5/00

[52] U.S. Cl. ..... Plt./18

[58] Field of Search ..... Plt./18, 26

*Primary Examiner*—Robert E. Bagwill

*Attorney, Agent, or Firm*—Charles W. Rummler

[57] ABSTRACT

A new and distinct variety of greenhouse rose plant which originated as a sport of the variety 'Sonia' (U.S. Plant Pat. No. 3,095) and is particularly distinguished by the very light pink coloration of the outer petals of the mature flower which gives it a generally Neyron Rose appearance except for the lower inside portion of the petals at the center of the fully opened bloom which contrasts considerably with respect to the Porcelain Rose and Begonia Rose coloration of the parent plant. This new rose plant variety blooms continuously and profusely the year around under greenhouse conditions with large flowers carried on sturdy, upright stems and with a flower peduncle having a length of about twelve centimeters, the blooms being long lasting on the plant and having a moderate lasting quality as a cut flower. The plant itself has a vigorous and upright growth habit with a free branching character and abundant foliage.

2 Drawing Sheets

BACKGROUND OF THE INVENTION

This new rose variety was discovered in a greenhouse of the Kanagawa Prefecture at Yokohama, Japan, on a rose plant of the variety 'Sonia' (U.S. Plant Pat. No. 3,095) and its much lighter and more delicate appearance then the parent plant caused me to select this sport for propagation and trial.

Propagation of this sport of the variety 'Sonia' was done by me by budding at the Prefecture of Kanagawa and the very satisfactory results indicated that this new plant could have very favorable commercial prospects. This caused me to continue propagation of this new plant by buds through successive generations, which demonstrated clearly that the novel characteristics of this new plant would true from generation to generation and appeared to be firmly fixed.

DESCRIPTION OF THE DRAWINGS

My new rose plant is illustrated by the accompanying photographic drawings, of which sheet one shows a full face view of the new flower with some of the foliage and sheet two shows in the upper view a series of buds in progressive stages of development, and in the lower view front and reverse side views of typical leaves, a bud, the base of a fully opened flower after the petals have been removed, a specimen of a floral stem, old and new wood, and typical thorns; the color rendition in all views being as nearly true as is reasonably possible to obtain by conventional photographic procedures.

DESCRIPTION OF THE NEW VARIETY

The following is a detailed description of my new rose as observed at the Kanagawa Prefecture at Yokohama, Japan, with color designations according to The R.H.S. Colour Chart published by The Royal Horticultural Society of London, England.

THE PLANT

Origin: Sport.

Parentage: 'Sonia' (U.S. Plant Pat. No. 3,095).

Classification:

*Botanic.*—Hybrid Floribunda.

*Commercial.*—Greenhouse Rose.

Form: Upright bush of medium height.

Growth habit: Vigorous, upright, sturdy and free branching.

Foliage:

*Quantity.*—Abundant.

*Number of leaves.*—3 to 5.

*Leaf size.*—About 80 mm. long and 55 mm. wide.

*Shape.*—Odd pinnate.

*Leaflets.*—Number: 3 or 5. Size: About 51 mm. long and 30 mm. wide. Shape: Oval with mucronate tip and dentate margins.

*Texture.*—Leathery.

*Aspect.*—Smooth and glossy.

*Color.*—Upper side — Green Group, 136A. Under side — Yellow-Green Group, 147B.

*Stipules.*—Thread-like.

*Petiolule.*—Length: About 2 mm.

*Rachis.*—About 5 mm. long on a leaf with 5 leaflets. About 26 mm. long on a leaf with 3 leaflets.

*Petioles.*—Length: About 22 mm.

*Ribs and veins.*—Depressed on upper leaf; slightly round on lower side.

*Thorns.*—Size: About 6 mm. Color: Grey-Brown Group, 199B, with a splash of Greyed Purple Group, 184D, on the upper edge.

THE BUD

Size: Medium.

*Diameter.*—About 55 mm.

*Length.*—About 36 mm.

Shape: Urn-shaped.

Rate of opening: Slow.

Color:

*When sepals first divide.*—Red Group, 49A, with Orange-White Group, 159C, at the base.

*When petals begin to unfurl.*—Red Group, 55D.

Sepals:

*Shape.*—Foliaceous with one small leaflet protruding on each side.

*Character.*—The sepals curl back when the flowers open.

*Color.*—Inside — Yellow-Green Group, 147D. Outside — Yellow-Green Group, 144A.

Calyx:

*Shape.*—Funnel-shaped.

*Size.*—Medium and of medium breadth.

*Splitting.*—The calyx does not split.

*Aspect.*—Smooth.

Peduncle:

*Length.*—About 120 mm. with small, slender spines.

*Character.*—Rigid, erect and double noded.

*Color.*—Yellow-Green Group, 144A.

THE FLOWER

Blooming habit: Continuous and profuse year around, blooming freely in fall and winter under greenhouse conditions.

Size: Large.

*Diameter.*—About 80 mm.

*Depth.*—About 55 mm.

Borne: Singly.

Shape:

*When bloom first opens.*—Cup-shaped.

*When bloom matures.*—Nicely imbricated.

Petalage:

*Number of petals.*—About 30 to 34.

*Arrangement.*—Imbricated.

*Form.*—Oval with mucronate tip.

*Texture.*—Leathery.

*Aspect.*—Satiny.

*Color.*—Outer petals: Body — Red Group, 55D. Base — Yellow-Green Group, 155C. Color Measurement — 43 mm. of 55D and 11 mm. of 155C. Reverse side: Body — Red Group, 56C. Base — Yellow-Green Group, 154D. Color Measurement — 38 mm. of 56C and about 16 mm. of 154D. Inside petals: Body — Red Group, 49A. Base — Yellow Group, 2B. Color Measurement — About 23 mm. of 49A and about 9 mm. of 2B. Reverse side: Body — Red Group, 52D. Base — Yellow Group, 4B. Color Measurement — About 25 mm. of 52D and about 7 mm. of 4B.

*Petaloids.*—Number: Four. Size: About 15 mm. Color: Red Group, 49A. Base — Yellow-Green Group, 2B.

Peduncle:

*Length.*—About 120 mm.

*Color.*—Yellow Group, 2B.

*Character.*—Sturdy and upright.

Discoloration after full bloom: None.

Persistence: The flower petals hang on and dry.

Disease resistance: Moderately resistant to mildew, rust, and black spots.

Lasting quality: Long lasting on the plant and moderate as a cut flower.

REPRODUCTIVE ORGANS

Stamens:

*Number.*—115.

*Arrangement.*—Slightly introrse.

*Anthers.*—Size: About 2 mm. Color: Yellow-Orange Group, 23D.

*Filaments.*—Length: About 7 mm. Color: Yellow Group, 9D.

*Pollen.*—Color: Yellow-Orange Group, 23D.

Pistils:

*Number.*—57.

*Styles.*—Length: About 10 to 13 mm. Color: Red Group, 54B.

*Stigmas.*—Color: Orange Group, 27B.

Character of ovaries: Medium funnel-shaped with rounded edges, flat in center and with silver threads covering the entire ovary.

I claim:

1. A new and distinctive rose plant and parts thereof, substantially as herein shown and described, characterized in particular by its very light pink, Neyron Rose-like coloration for the outer petals and a Dawn Pink coloration at the base of the central petals; and by its profuse and continuous production of flowers of large size, and its vigorous, sturdy and upright growth habit.

* * * * *

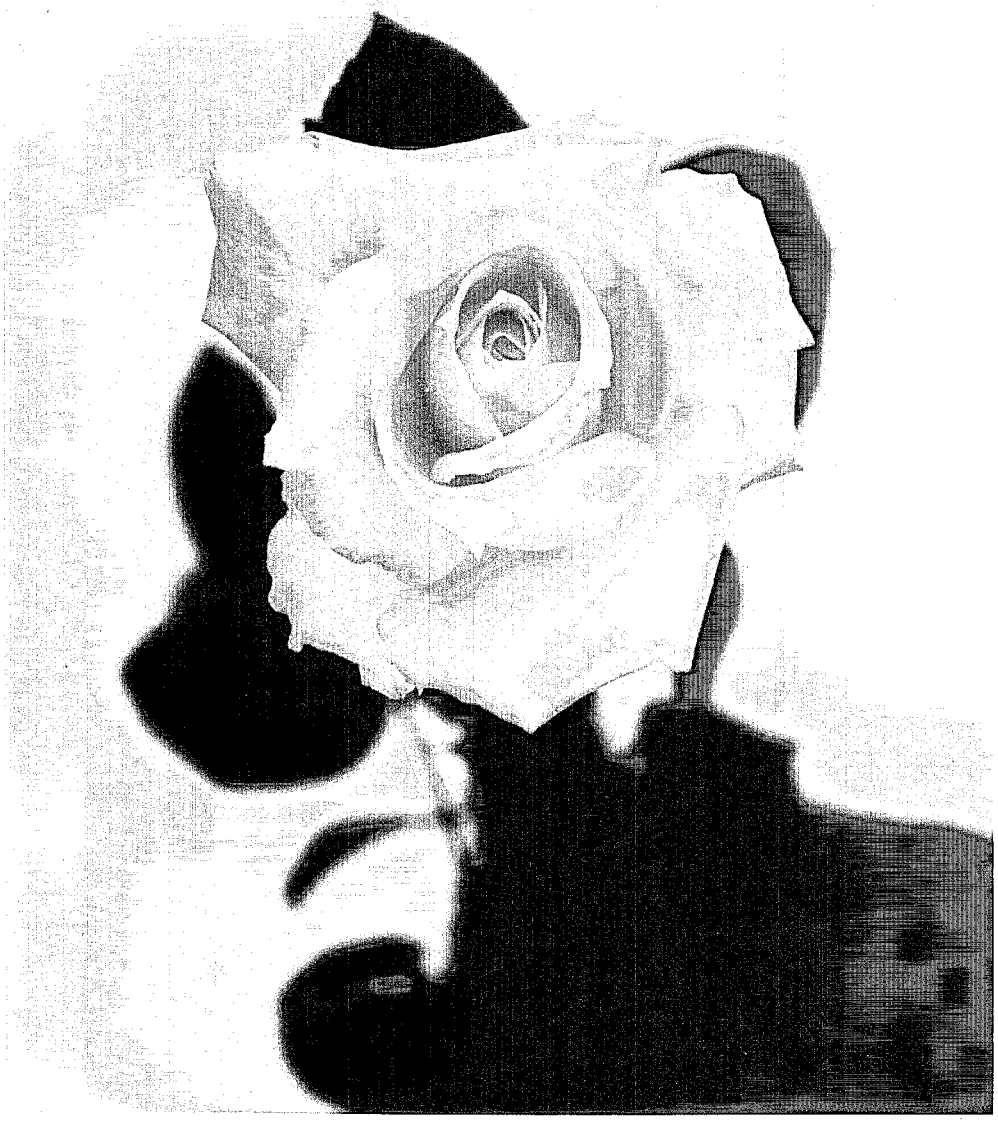

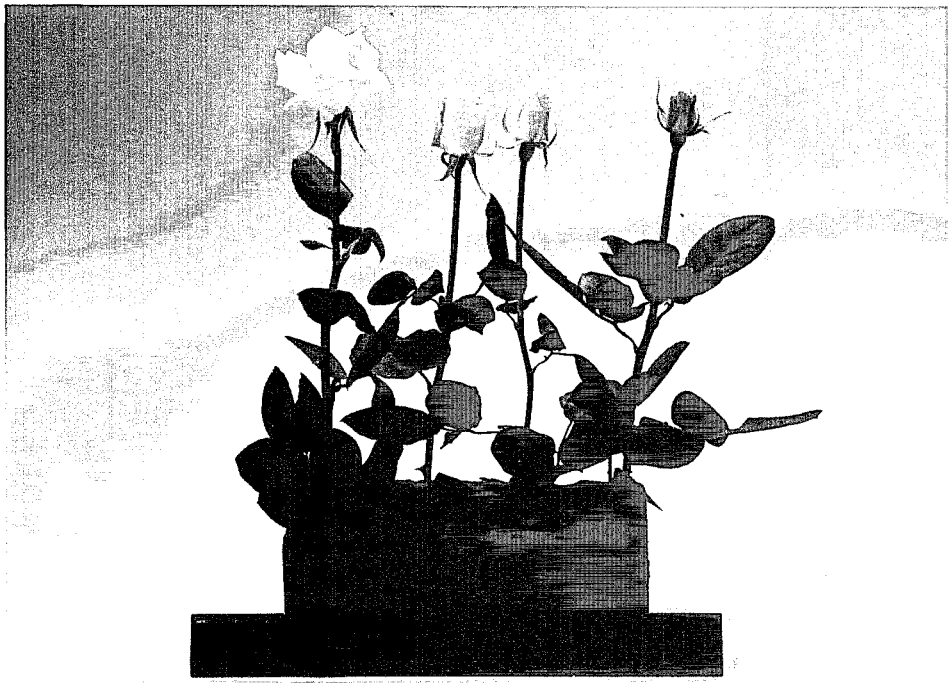
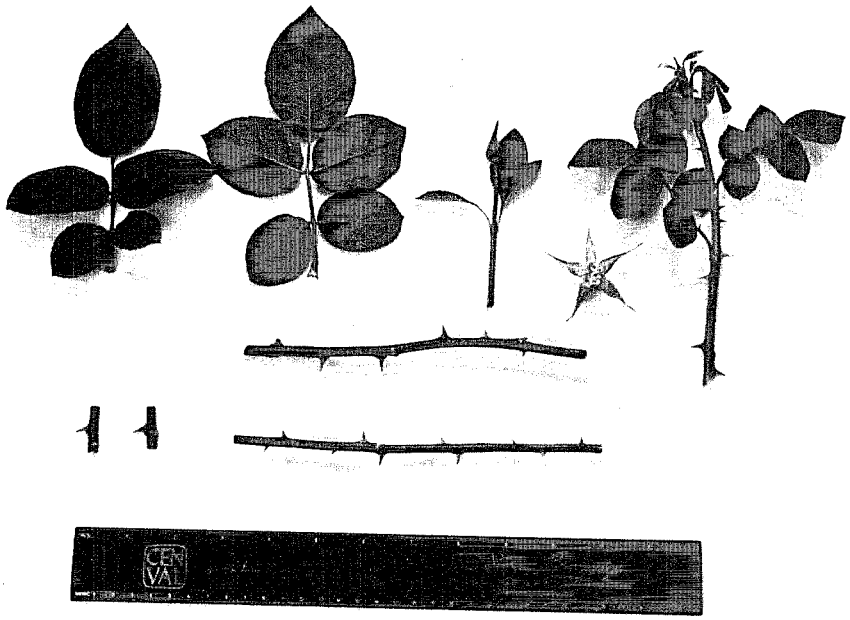
CEN
VAL